US00PP16445P2

(12) United States Plant Patent
Smith

(10) Patent No.: US PP16,445 P2
(45) Date of Patent: Apr. 18, 2006

(54) *CHRYSANTHEMUM* PLANT NAMED 'YOKRISTI'

(50) Latin Name: *Chrysanthemum×morifolium*
Varietal Denomination: Yokristi

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 178 days.

(21) Appl. No.: 10/937,764

(22) Filed: Sep. 8, 2004

(51) Int. Cl.
*A01H 5/00* (2006.01)

(52) U.S. Cl. ..... Plt./289

(58) Field of Classification Search ..... Plt./289
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Yokristi', characterized by its upright, outwardly spreading and rounded plant habit; freely branching habit; freely flowering habit; decorative-type inflorescences with elongated oblong-shaped ray florets; yellow-colored ray florets; natural season flowering in mid-October in the Northern Hemisphere; and good garden performance.

2 Drawing Sheets

Figure 1:
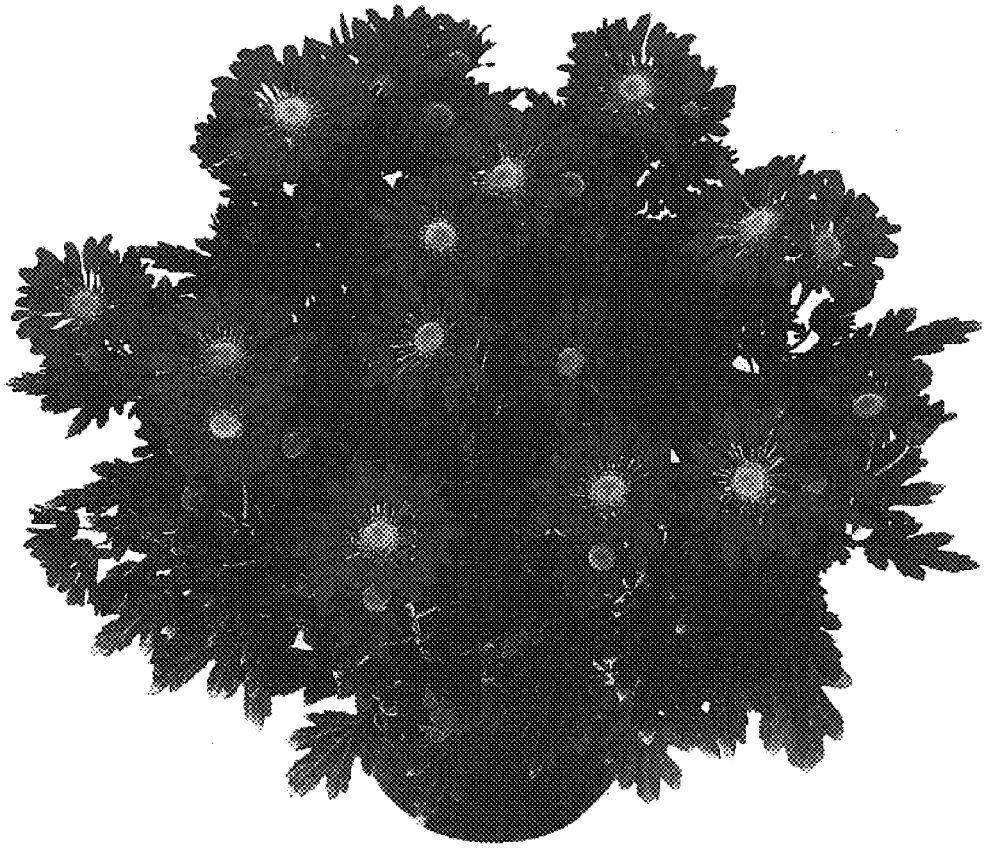
Figure 2:
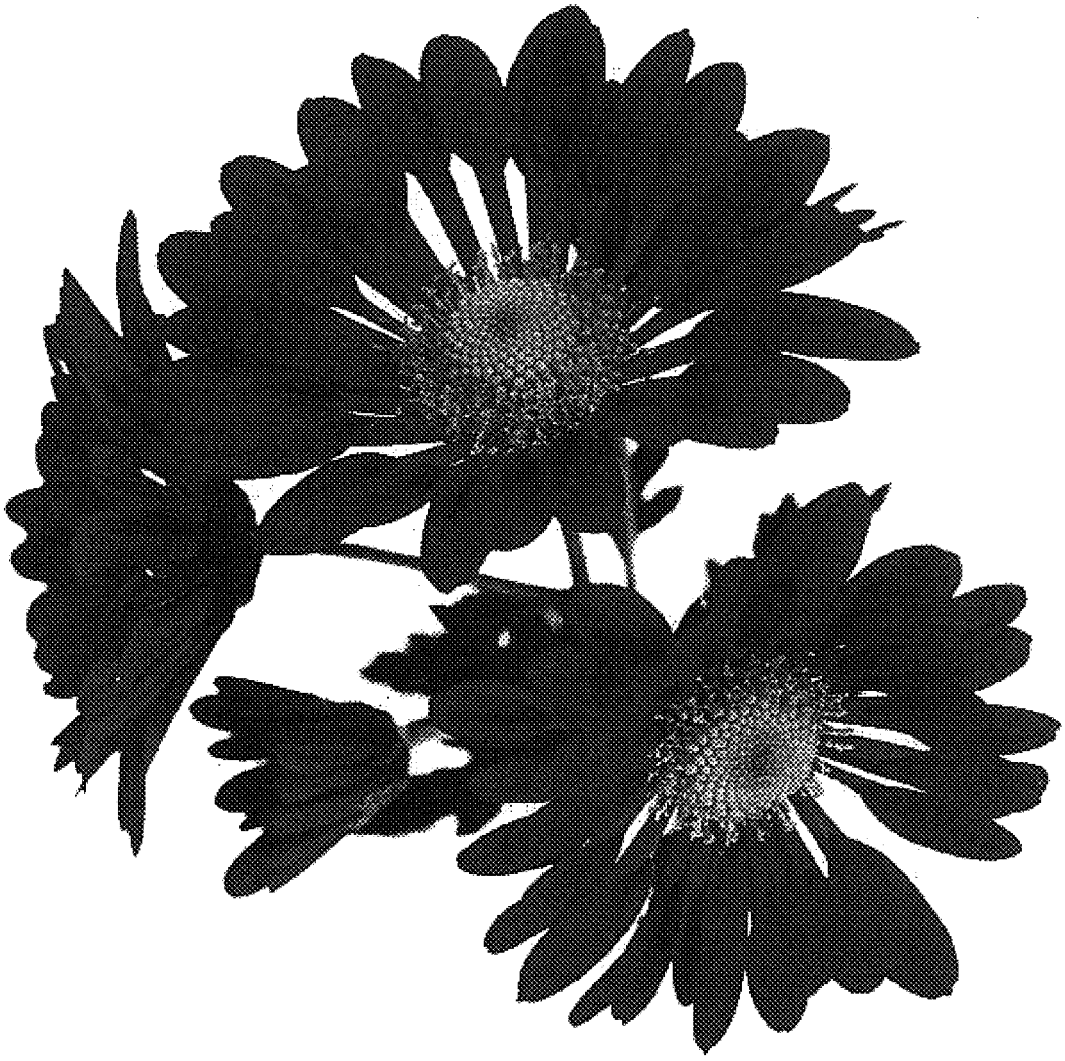

Botanical classification/cultivar designation: *Chrysanthemum×morifolium* cultivar Yokristi.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Yokristi'.

The new cultivar is a product of a planned breeding program conducted by the Inventor in Salinas, Calif. and Alva, Fla. The objective of the breeding program is to create new garden-type *Chrysanthemum* cultivars having inflorescences with desirable inflorescence forms, attractive floret coloration and good garden performance.

The new *Chrysanthemum* originated from a cross-pollination made in December, 1999 in Salinas, Calif., of a proprietary *Chrysanthemum×morifolium* seedling selection identified as code number 97-L037, not patented, as the female, or seed, parent with a proprietary *Chrysanthemum×morifolium* seedling selection identified as code number 96-L236, not patented, as the male, or pollen, parent. The new *Chrysanthemum* was discovered and selected by the Inventor as a single flowering plant within the progeny of the stated cross-pollination grown in a controlled environment in Alva, Fla. in November, 2000. The selection of this plant was based on its desirable inflorescence form, attractive floret coloration and good garden performance.

Asexual reproduction of the new cultivar by terminal vegetative cuttings in a controlled environment in Alva, Fla. since January, 2001, has shown that the unique features of this new *Chrysanthemum* are stable and reproduced true to type in successive generations.

SUMMARY OF THE INVENTION

The cultivar Yokristi has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yokristi'. These characteristics in combination distinguish 'Yokristi' as a new and distinct cultivar of *Chrysanthemum:*

1. Upright, outwardly spreading and rounded plant habit.
2. Freely branching habit.
3. Freely flowering habit.
4. Decorative-type inflorescences with elongated oblong-shaped ray florets.
5. Yellow-colored ray florets.
6. Natural season flowering in mid-October in the Northern Hemisphere.
7. Good garden performance.

In side-by-side comparisons conducted in Alva, Fla. under natural season conditions, plants of the new *Chrysanthemum* differed from plants of the female parent, the proprietary seedling selection identified as code number 97-L037, in the following characteristics:

1. Plants of the new *Chrysanthemum* were more rounded than plants of the female parent selection.
2. Plants of the new *Chrysanthemum* flowered about two weeks later than plants of the female parent selection.

In side-by-side comparisons conducted in Alva, Fla. under natural season conditions, plants of the new *Chrysanthemum* differed from plants of the male parent, the proprietary seedling selection identified as code number 96-L236, in the following characteristics:

1. Plants of the new *Chrysanthemum* were smaller and more rounded than plants of the male parent selection.
2. Plants of the new *Chrysanthemum* flowered more uniformly than plants of the male parent selection.
3. Plants of the new *Chrysanthemum* flowered about ten days later than plants of the male parent selection.
4. Plants of the new *Chrysanthemum* and the male parent selection differed in ray floret coloration as plants of the male parent selection had white-colored ray florets.

Plants of the new *Chrysanthemum* can be compared to plants of the *Chrysanthemum* cultivar Draga, not patented. In side-by-side comparisons conducted in Alva, Fla. under natural season conditions, plants of the new *Chrysanthemum* differed from plants of the cultivar Draga in the following characteristics:

1. Plants of the new *Chrysanthemum* were smaller than plants of the cultivar Draga.
2. Plants of the new *Chrysanthemum* had smaller inflorescences than plants of the cultivar Draga.
3. Plants of the new *Chrysanthemum* flowered about five days later than plants of the cultivar Draga.

Plants of the new *Chrysanthemum* can also be compared to plants of the *Chrysanthemum* cultivar Gedi Two Fio, disclosed in U.S. Plant Pat. No. 14,399. In side-by-side comparisons conducted in Alva, Fla. under natural season conditions, plants of the new *Chrysanthemum* differed from plants of the cultivar Gedi Two Fio in the following characteristics:

1. Plants of the new *Chrysanthemum* were smaller than plants of the cultivar Gedi Two Fio.
2. Plants of the new *Chrysanthemum* had larger inflorescences than plants of the cultivar Gedi Two Fio.
3. Plants of the new *Chrysanthemum* and the cultivar Gedi Two Fio differed in ray floret cororation as plants of the cultivar Gedi Two Fio had orange-colored ray florets.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photograhs may differ slightly from the color values cited in the detailed botanical description which accurately describe the colors of the new *Chrysanthemum.*

The photograph on the first sheet comprises a side perspective view of a typical flowering plant of 'Yokristi' grown in a container.

The photograph on the second sheet comprises a close-up view of typical inflorescences of the cultivar 'Yokristi'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and fall in an outdoor nursery and under conditions and practices which approximate those generally used in commercial garden-type *Chrysanthemum* production. One cutting was planted in a 15.25-cm container in mid-July. During the production of the plants, plants were exposed to natural season photoperiodic conditions with day temperatures averaging 26° C. and night averaging 18° C. Measurements and numerical values represent averages for typical flowering plants.

Botanical classification: *Chrysanthemum×morifolium* cultivar Yokristi.

Commercial classification: Decorative-type garden *Chrysanthemum.*

Parentage:

*Female, or seed, parent.*—Proprietary *Chrysanthemum×morifolium* seedling selection identified as code number 97-L037, not patented.

*Male, or pollen, parent.*—Proprietary *Chrysanthemum×morifolium* seedling selection identified as code number 96-L236, not patented.

Propagation:

*Type.*—Terminal vegetative cuttings.

*Time to initiate roots, year-round.*—About four days at 21° C.

*Time to produce a rooted cutting, year-round.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with rounded crown. Stems initially upright, than outwardly spreading. Freely branching with lateral branches potentially developing at every node. Moderately vigorous to vigorous.

*Plant height.*—About 19.25 cm.

*Plant diamenter.*—About 33.5 cm.

*Lateral branches.*—Length: About 19 cm. Diameter: About 5 mm. Internode length: About 1.3 cm. Strength: Strong. Texture: Pubescent. Color: Close to 144A.

*Foliage description.*—Leaf arrangement: Alternate. Length: About 3.4 cm. Width: About 3.5 cm. Apex: Mucronate. Base: Mostly truncate. Margin: Palmately and deeply lobed; sinuses parallel to divergent. Texture, upper and lower surfaces: Pubescent. Color: Developing foliage, upper surface: More green than 147A. Developing foliage, lower surface: Close to 147B. Fully expanded foliage, upper surface: Close to 147A. Fully expanded foliage, lower surface: Close to 147B. Venation, upper surface: Close to 147A. Venation, lower surface: Close to 146A. Petiole: Length: About 1 cm. Diameter: About 3 mm. Texture, upper and lower surfaces: Pubescent. Color, upper surface: 147A to 146A. Color, lower surface: Close to 146A.

Infloresence description:

*Appearance.*—Decorative-type inflorescence form with elongated oblong-shaped ray florets. Inflorescences borne on terminals above foliage, arising from leaf axils. Disc and ray florets developing acropetally on a capitulum. Inflorescences face mostly upright or outwardly. Inflorescences hemispherical in shape. Freely flowering habit; about 25 inflorescences and develop per lateral branch. Inflorescences persistent. Inflorescences not fragrant.

*Flowering response.*—Under natural season conditions, plants flower in mid-October in the Northern Hemisphere.

*Inflorescence bud (before showing color).*—Height: About 7 mm. Diameter: About 6 mm. Shape: Oblate. Color (lower surface of phyllaries): Close to 146A.

*Inflorescence size.*—Diameter: About 4.75 cm. Depth (height): About 2.25 cm. Disc diameter: Disc florets not observed. Receptacle diameter: About 5 mm. Receptacle height: About 5 mm.

*Ray florets.*—Shape: Elongated oblong. Length: About 2.3 cm. Corolla tube length: About 3 mm. Width: About 7 mm. Apex: Acute to emarginate. Margin:

Fused. Texture: Smooth, glabrous; satiny. Surface: Concave. Orientation: Initially upright, than perpendicular to the peduncle. Number of ray florets per inflorescence: About 160 in numerous whorls. Color: When opening, upper and lower surfaces: Close to 6A. Fully opened, upper surface: Close to 6A to 6B. Fully opened, lower surface: Close to 6B to 6C.

*Phyllaries.*—Quantity per inflorescence: About 22. Length: About 5.5 mm. Width: About 3 mm. Shape: Deltoid, elongated. Apex: Acute. Base: Truncate, fused. Margin: Entire. Texture, upper surface: Smooth, waxy. Texture, lower surface: Pubescent. Color, upper surface: Close to 144A. Color, lower surface: Close to 146A.

*Peduncle.*—Length: First peduncle: About 4.1 cm. Fourth peduncle: About 6.75 cm. Seventh peduncle: About 9.4 cm. Diameter: About 2 mm. Strength: Strong. Aspect: About 50° from vertical. Texture: Pubescent. Color: Close to 144A.

*Reproductive organs.*—Androecium: None observed. Gynoecium: Present on ray florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be have good garden performance and to be tolerant to rain, wind and temperatures ranging from 0 to greater than 38° C.

It is claimed:

1. A new and distinct cultivar of *Chrysanthemum* plant named 'Yokristi', as illustrated and described.

* * * * *